US008580539B2

(12) United States Patent  
Korlach

(10) Patent No.: US 8,580,539 B2  
(45) Date of Patent: Nov. 12, 2013

(54) PHOSPHOLINK NUCLEOTIDES FOR SEQUENCING APPLICATIONS

(71) Applicant: Pacific Biosciences of California, Inc., Menlo Park, CA (US)

(72) Inventor: Jonas Korlach, Newark, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

(21) Appl. No.: 13/731,493

(22) Filed: Dec. 31, 2012

(65) Prior Publication Data

US 2013/0122490 A1    May 16, 2013

Related U.S. Application Data

(62) Division of application No. 12/620,293, filed on Nov. 17, 2009, now Pat. No. 8,367,813.

(60) Provisional application No. 61/115,381, filed on Nov. 17, 2008.

(51) Int. Cl.
*C12P 19/34* (2006.01)
*C12Q 1/68* (2006.01)

(52) U.S. Cl.
USPC .......................................... 435/91.1; 435/6.1

(58) Field of Classification Search
USPC .................................................. 435/6.1, 91.1
See application file for complete search history.

(56) References Cited

U.S. PATENT DOCUMENTS

| 5,882,863 | A | 3/1999 | Imai et al. |
|---|---|---|---|
| 6,917,726 | B2 | 7/2005 | Levene et al. |
| 7,056,661 | B2 | 6/2006 | Korlach et al. |
| 7,504,215 | B2 | 3/2009 | Cole et al. |
| 7,968,702 | B2 | 6/2011 | Wegener et al. |
| 2003/0044781 | A1 | 3/2003 | Korlach et al. |
| 2003/0124576 | A1 | 7/2003 | Kumar et al. |
| 2007/0072196 | A1 | 3/2007 | Xu et al. |
| 2009/0004666 | A1 | 1/2009 | Tanabe et al. |
| 2009/0186343 | A1 | 7/2009 | Wang et al. |
| 2011/0165652 | A1 | 7/2011 | Hardin et al. |
| 2011/0177496 | A1 | 7/2011 | Williams et al. |

OTHER PUBLICATIONS

Ansorge et al., "Automated DNA sequencing: ultrasensitive detection of fluorescent bands during electrophoresis", *Nucleic Acids Res.* 15(11): 4593-602 (1987).

Connell, C. et al., "Automated DNA Sequence Analysis", *BioTechniques*, 5(4): 342-84 (1987).

Driscoll, R. J. et al., "Atomic-Scale Imaging of DNA Using Scanning Tunneling Microscopy", *Nature*, 346(6281): 294-296 (1990).

Eggeling, C. et al., "Data registration and selective single-molecule analysis using multi-parameter fluorescence detection", *Journal of Biotechnology*, 86: 163-180 (2001).

Földes-Papp, Z. et al., "Fluorescently labeled model DNA sequences for exonucleolytic sequencing", *Journal of Biotechnology* 86: 203-224 (2001).

(Continued)

*Primary Examiner* — Jezia Riley
(74) *Attorney, Agent, or Firm* — Morgan, Lewis & Bockius LLP

(57) ABSTRACT

The present invention provides labeled phospholink nucleotides that can be used in place of naturally occurring nucleotide triphosphates or other analogs in template directed nucleic acid synthesis reactions and other nucleic acid reactions and various analyses based thereon, including DNA sequencing, single base identification, hybridization assays, and others.

15 Claims, 5 Drawing Sheets

(56) References Cited

OTHER PUBLICATIONS

Földes-Papp, Z. et al., "Fluorescent high-density labeling of DNA: error-free substitution for a normal nucleotide", *Journal of Biotechnology* 86: 237-253 (2001).

Goodwin, P.M. et al., "Application of Single Molecule Detection to DNA Sequencing", *Nucleosides & Nucleotides*, 16(56): 543-550 (1997).

Grabarek, Z. and Gergely, J., "Zero-Length Crosslinking Procedure with the Use of Active Esters", *Analyt Biochem*, 185:131-135 (1990).

Hinz, M. et al., "Polymer support for exonucleolytic sequencing", *Journal of Biotechnology*, 86: 281-288 (2001).

Howorka, S. et al., "Sequence-Specific Detection of Individual DNA Strands Using Engineered Nanopores", *Nature Biotechnology*, 19(7): 636-639 (2001).

Meller, A. et al., "Rapid Nanopore Discrimination Between Single Polynucleotide Molecules", *Proceedings of the National Academy of Sciences of the United States of America*, 97(3): 1079-1084 (2000).

Prober et al., "A System for Rapid DNA Sequencing with Fluorescent Chain-Terminating Dideoxynucleotides", *Science*, 238:336-41 (1997).

Rigler et al., "DNA-Sequencing at the Single Molecule Level", *Journal of Biotechnology*, 86(3): 161 (2001).

Sauer, M. et al., "Single molecule DNA sequencing in submicrometer channels: state of the art and future prospects", *Journal of Biotechnology*, 86: 181-201 (2001).

Seela, F. et al., "Fluorescent DNA: the development of 7-deazapurine nucleoside triphosphates applicable for sequencing at the single molecule level", *Journal of Biotechnology*, 86: 269-279 (2001).

Smith, L. et al., "Fluorescence detection in automated DNA sequence analysis", *Nature*, 321:674 (1986).

Staros and Swing, "Enhancement by *N*-Hydroxysulfosuccinimide of Water-Soluble Carbodimide-Mediated Coupling Reactions", *Analyt Biochem*, 156:220-222 (1986).

Stephan, J. et al., "Towards a general procedure for sequencing single DNA molecules", *Journal of Biotechnology*, 86: 255-267 (2001).

PHOSPHOLINK NUCLEOTIDES FOR SEQUENCING APPLICATIONS

CROSS REFERENCE TO RELATED APPLICATIONS

This application is a division of U.S. patent application Ser. No. 12/620,293 filed Nov. 17, 2009 which claims priority to Provisional U.S. Patent Application No. 61/115,381, filed Nov. 17, 2008, the full disclosure of which is incorporated herein by reference in its entirety for all purposes.

BACKGROUND OF THE INVENTION

For nucleic acid analyses based upon detection of polymerase-mediated incorporation of nucleotides, the label on the detectable nucleotides can have a significant impact on the efficiency and accuracy of such analyses. Fluorophore-labeled nucleotides are generally used in such nucleic acid analyses. However, traditional methods of labeling nucleotides with fluorophores can pose problems with respect to lack of brightness of the label, photodamage to the polymerase, and instability of the label due to photobleaching. In addition, such fluorophore-labeled nucleotides can require the use of expensive equipment, such as high power lasers, electron multiplying CCD cameras, and the like. As such, brighter, more robust labels for sequencing applications are desirable.

SUMMARY OF THE INVENTION

Accordingly, the present invention provides nucleotides labeled with beads that produce a brighter signal than is generally achievable with traditional methods of labeling nucleotides.

In one aspect, the invention provides a composition that includes a labeled phospholink nucleotide. In this aspect, the labeled phospholink nucleotide includes a structure that has formula:

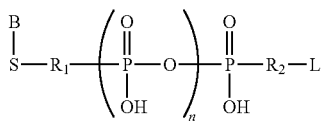

wherein B is a nucleobase; S is a sugar moiety; L is a bead comprising a fluorophore; $R_1$ is selected from oxygen and sulfur; $R_2$ is a linker moiety; and n is an integer selected from 0 to 9.

In one aspect, the invention provides a composition comprising a microfluidic flow cell. In a further aspect, the microfluidic flow cell includes a substrate with a surface, and a nucleic acid polymerase is immobilized on the surface of the substrate. In a still further aspect, the microfluidic flow cell further includes at least four differentially labeled nucleotides, wherein the labeled nucleotides include beads comprising fluorophores.

In one aspect, the invention provides a method of determining an identity of a nucleotide in a template nucleic acid sequence. Such a method includes the steps of (i) providing the template nucleic acid sequence complexed with a polymerase enzyme capable of template dependent synthesis of a complementary nascent sequence as a first complex; (ii) contacting the first complex with a labeled phospholink nucleotide, wherein the labeled phospholink nucleotide includes a bead with at least one fluorophore, and wherein the labeled phospholink nucleotide is complementary to a known nucleotide; and (iii) detecting whether the labeled phospholink nucleotide is incorporated into the nascent sequence. In this aspect, incorporation of the labeled phospholink nucleotide is indicative that the complementary nucleotide is in a position in the template nucleic acid that is being processed by the polymerase enzyme.

In one aspect, the invention provides a nucleic acid sequencing system. Such a system includes: (i) a body structure with a plurality of microfluidic channels; (ii) a source of one or more template nucleic acids; (iii) a source of one or more sequencing reagents; and (iv) a fluid flow controller that flows the template nucleic acid and the one or more sequencing reagents into contact in the at least first microfluidic channel. In a further aspect, the template nucleic acid source is capable of being fluidly coupled to at least a first one of the microfluidic channels. In a still further aspect, the sequencing reagent source is capable of being fluidly coupled to the at least first microfluidic channel. In a still further aspect, the source of the one or more sequencing reagents includes a set of at least four differently labeled nucleotide analogs, and the labeled nucleotide analogs include a fluorescent bead. In a further aspect, the nucleic acid sequencing system includes a detector. In a still further aspect, the nucleic acid sequencing system forms one or more sequencing products and the detector detects the one or more sequencing products, thereby determining at least a subsequence of the template nucleic acid.

BRIEF DESCRIPTION OF THE DRAWINGS

FIG. 2A illustrates a bead-labeled phospholink nucleotide with an aminohexyl linker. FIG. 2B illustrates a bead-labeled phospholink nucleotide with a linker comprising two aminohexyl groups. FIG. 2C illustrates a bead-labeled phospholink nucleotide with a linker comprising an aminohexyl linker and a chain of poly(ethylene glycol) groups.

FIG. 5A shows the absorbance at 265 nm of two different types of phospholink nucleotides as a function of number of washes, and FIG. 5B shows the absorbance spectra of different bead-labeled phospholink nucleotides after 7 washes.

DETAILED DESCRIPTION OF THE INVENTION

Overview

Figure 1:
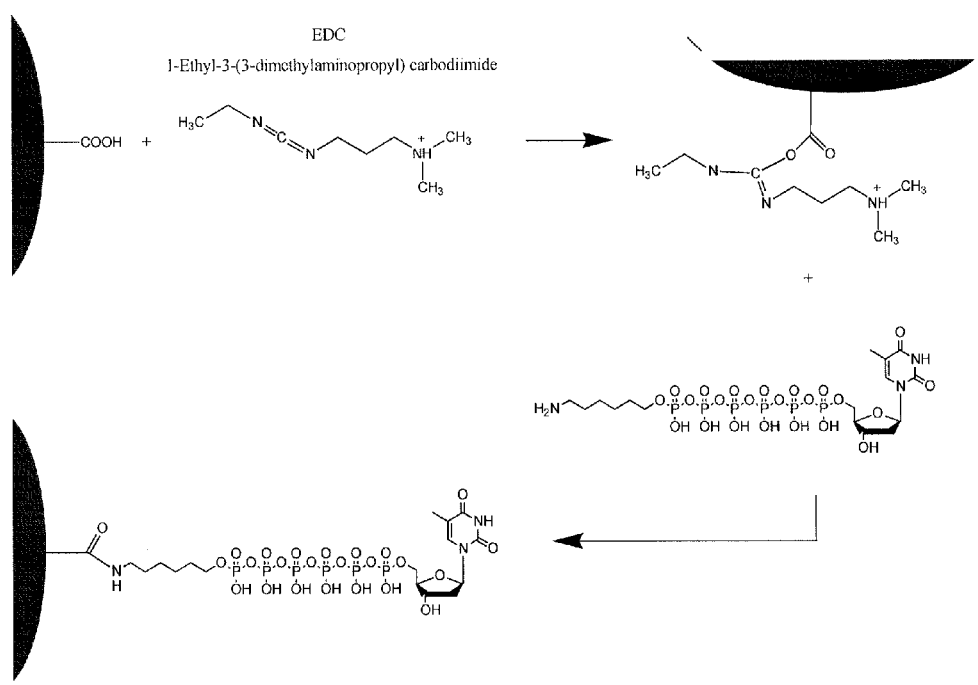
FIG. 1 illustrates an exemplary method for coupling a phospholink nucleotide to a bead.

The present invention provides methods and compositions for sequencing applications utilizing nucleoside polyphosphates labeled with detectable beads. In one embodiment, the nucleotides of the invention are labeled with fluorescent beads. Such beads provide an advantage over labels generally used in the art, because instead of the normal 1:1 ratio between a fluorescent label and a nucleotide, fluorescent beads can comprise multiple fluorophores, resulting in a much brighter signal for every labeled nucleotide. A further advantage to such fluorescent beads comprising multiple fluorophores is that the signal from such beads is unlikely to be reduced to background levels. Conventional organic fluorophores blink, which can introduce apparent insertion errors (false positives) in sequencing applications. Since beads comprising multiple fluorophores are highly likely to have at least one fluorophore always emitting fluorescence, any reduction in signal that may occur due to one fluorophore blinking is averaged out over the multiple fluorophores carried by a particular bead. The multiple fluorophores also reduce the effects of photobleaching, because even if one fluorophore photobleaches, the other fluorophores are likely to continue emitting a signal. Fluorescent beads comprising multiple fluorophores thus provide a significantly improved signal relative to labels comprising only a single fluorophore.

A further advantage of the fluorescent beads used in accordance with the present invention is that multiple nucleoside polyphosphates can be attached to these beads, which allows for "recycling" of these beads through multiple incorporation events, because when one nucleoside polyphosphate is incorporated into the nascent chain and then subsequently cleaved from the bead, the remaining nucleoside polyphosphates joined to the bead are still available for subsequent incorporation events. This also results in a reduction of the apparent binding affinity between the nucleotide-bead conjugates to the enzyme, allowing lower background signal, and thus higher signal-to-noise ratios. In a further embodiment, the detectable beads are joined to each nucleoside polyphosphate through a terminal phosphate of the nucleoside polyphosphate.

Labeled Phospholink Nucleotides

The term "phospholink nucleotides" is generally used herein to refer to nucleoside polyphosphates that can be linked to a label through a terminal phosphate group. Unless otherwise noted, the term "phospholink nucleotide" and "nucleotide" are used interchangeably herein.

In one aspect, the invention provides a labeled phospholink nucleotide that includes a structure according to the general formula:

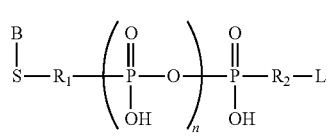

in which B represents a natural or non-natural nucleobase or nucleobase analog; S is a sugar moiety, an acyclic moiety or a carbocyclic moiety; L is a detectable label, $R_1$ is selected from oxygen and sulfur, $R_2$ is a linker moiety, and n is an integer selected from 0 to 9. It should be noted that $R_2$ is not a required element of labeled phospholink nucleotide of the invention, and that the label "L" may also optionally include a linker moiety.

In one embodiment, the linker group $R_2$ comprises one or more groups such that the compound represented by formula (I) is a nucleoside polyphosphate analog. For example, $R_2$ may comprise one or more phosphonate groups, brominated phosphate groups, and the like.

The nucleobase represented by "B" in Formula (I) can be selected from any of the natural or non-natural nucleobases or nucleobase analogs, including e.g., purine or pyrimidine bases that are routinely found in nucleic acids and nucleic acid analogs, including adenine, thymine, guanine, cytidine, uracil, and in some cases, inosine. The nucleobases of the present invention may include the conventional bases described herein or they may include such bases substituted at one or more side groups, or other analogs, such as 1, N-6-ethenoadenosine or pyrrolo C, in which an additional ring structure renders the nucleobase neither a purine nor a pyrimidine.

The S group of Formula (I) can be a sugar moiety that provides a suitable backbone for synthesizing a nucleic acid strand. In one aspect, the sugar moiety is selected from D-ribosyl, 2' or 3' D-deoxyribosyl, 2'3'-D-dideoxyribosyl, 2',3'-D-didehydrodideoxyribosyl, 2' or 3' aminoribosyl, 2' or 3' mercaptoribosyl, 2' or 3' alkothioribosyl, acylcic, carbocyclic, or other modified sugar moieties. In a further aspect, a variety of carbocyclic or acyclic moieties can be incorporated into the S group in place of a sugar moiety, including e.g., those described in published U.S. Pat. No. 7,041,812, which is incorporated herein by reference in its entirety for all purposes, and in particular for its teachings regarding alternative moieties that can be used in place of a sugar moiety.

As discussed further herein, "L" in Formula (I) is a detectable label. In one aspect, L is a bead comprising one or more detectable moieties, including without limitation: luminescent, chemiluminescent, fluorescent, fluorogenic, chromophoric, magnetic, light scattering, and/or chromogenic moieties.

Further details regarding the detectable label "L" and the linker moiety "R" are provided herein.

Bead-labeled Phospholink Nucleotides

In one aspect, the present invention provides phospholink nucleotides labeled with beads. In one embodiment, such beads comprise fluorophores. In further embodiments, the fluorophores are embedded in a material contained in or associated with the beads. Although for clarity's sake the following embodiments of the invention are described in terms of nucleotides linked to fluorescent beads, it will be appreciated that the present invention also encompasses nucleotides linked with beads comprising other kinds of detectable labels, including without limitation dyes (including surface-bound dyes on metal nanoparticles with or without fluorescent enhancements), chromophores, enzymes, antigens, heavy metals, magnetic probes, phosphorescent groups, radioactive materials, chemiluminescent moieties, scattering or fluorescent nanoparticles, fluorescein labels, rhodamine labels, cyanine labels (i.e., Cy3, Cy5, and the like, generally available from the Amersham Biosciences division of GE Healthcare), the Alexa Fluor® family of fluorescent dyes (available from Invitrogen, Inc.) and other fluorescent and fluorogenic dyes. Such labels are known in the art and are disclosed for example in Prober, et. al., Science 238: 336-41 (1997); Connell et. al., BioTechniques 5(4): 342-84 (1987); Ansorge, et. al., Nucleic Acids Res. 15(11): 4593-602 (1987); and Smith et. al., Nature 321:674 (1986), which are hereby incorporated by reference in their entirety for all purposes and in particular for their teachings regarding such labels.

It will be appreciated that the term "bead" as used herein refers to any particle that can be joined to phospholink nucleotides according to the present invention. Such beads include without limitation latex beads, glass beads, polymeric beads, metal nanoparticles, magnetic nanoparticles, and avidin particles. Beads of the invention may further include without limitation inorganic materials, such as semiconductor nanoparticles, including e.g., II-V and II-VI core shell nanocrystals and the like. As will be appreciated, although the term bead encompasses spherical objects, any shape and size of bead can be used in accordance with the present invention.

In one embodiment, nucleotides are joined to beads of diameters ranging from about 5 nm to about 1 μm. In a further embodiment, beads of use in the invention have diameters ranging from about 10 nm to about 500 nm, from about 15 nm to about 400 nm, from about 20 nm to about 300 nm, from about 30 nm to about 200 nm, from about 40 nm to about 100 nm, and from about 50 nm to about 75 nm. Beads of the invention will generally be spherical in shape, but beads of other shapes are also encompassed by the present invention.

In a further aspect, bead-labeled phospholink nucleotides of the invention are encapsulated in order to block damage to the fluorophores in the beads from radicals that can be generated during illuminated reactions. The beads may be encapsulated in organic or inorganic materials, including, e.g., latex, polymeric materials such as polyethylene glycols, alginates, and the like, and other matrices. Such encapsulation can increase the read-length of sequencing reactions utilizing such bead-labeled phospholink nucleotides by alleviating and preventing photodamage, particularly the detrimental effects from free radicals that can be generated from illumination of fluorophores. In particular, encapsulation of fluorophores in beads and then optionally further encapsulation of the beads in latex, polymers, and/or other matrices, isolates those fluorophores from the environment and prevent free radicals, including free radical oxygen species, that can cause damage to reactants in a sequencing reaction, including polymerases used in sequencing-by-synthesis reactions. By limiting damage to polymerases, the read length of sequencing reactions utilizing such polymerases can be increased.

Although for clarity's sake much of the discussion herein will be with respect to beads comprising fluorophores, it will be appreciated that the methods and compositions of the present invention are not limited to fluorescent beads and encompass any bead with any detectable label, as described further above.

Fluorescent Beads Comprising Multiple Fluorophores

Fluorescent beads for use in the present invention generally comprise multiple fluorophores. Such beads will generally provide a brighter and more robust signal than is possible with conventional fluorescent labels. Conventional organic fluorophores blink, which can decrease the signal and introduce apparent insertion errors when used in sequencing applications. In contrast, the signal from beads carrying multiple fluorophores will not show a decreased signal due to blinking, because there is an increased likelihood that at least one fluorophore is emitting fluorescence at all times.

Fluorescent beads comprising multiple fluorophores also provide a more robust signal than is possible with conventional fluorophore labels, because the signal of such beads is resistant to the effects of photobleaching. Photobleaching is an exponential process with respect to the time a fluorophore is emitting light, which means that some fluorophores photobleach before enough photons have been emitted to allow them to be detected reliably. Beads containing multiple fluorophores alleviate or eliminate this problem, because it is likely that at least one fluorophore will not photobleach and will be able to emit a signal.

In one exemplary embodiment, all of the fluorophores contained in beads of the invention have the same color.

In one exemplary embodiment, a bead of the invention will comprise different types of fluorophores (i.e., different colors). Such beads allow mixing of colors in sequencing applications, which has the advantage of requiring fewer separation channels. For example, a set of bead-labeled nucleotides may include beads with only green dyes, beads with only red dyes, and beads with half green/half red (which would appear yellow). Such a set of beads would reduce the number of channels needed for detection to just 2, because the three different kinds of beads would give (0,1), (1,0) and (½, ½) signal strength for the three beads respectively. A separate detection channel would thus not be needed for each fluorophore color.

Attachment of Phospholink Nucleotides to Beads

In one embodiment, beads of use in the invention comprise surfaces derivatized with functional groups. In a further embodiment, such functional groups are activated and then subsequently coupled to an amino-terminated nucleotide or nucleotide analog. Non-limiting examples of functional groups of use in beads of the invention include carboxyl, amine, sulfate, aldehyde and thiol groups.

An exemplary mechanism for coupling a bead (also referred to herein as a "nanosphere" or "particle") to a phospholink nucleotide is illustrated in FIG. 1. As shown in FIG. 1, a bead with a carboxyl-terminated surface can be activated by 1-Ethyl-3-(3-dimethylaminopropyl) caroboiimide and then subsequently coupled to an aminoterminated nucleotide analog, which in this illustration is a nucleotide hexaphosphate. Although a single phospholink nucleotide is shown coupled to the bead in FIG. 1, it will be appreciated that numerous phospholink nucleotides can be similarly coupled to the same bead through this and similar methods.

In another exemplary embodiment, nucleotides joined to biotin are joined to avidin particles through an interaction between biotin and avidin, thus coupling the nucleotide to the particle. Multiple biotin-phospholink nucleotides can be attached to avidin particles. Such biotin-avidin linkages are well known and characterized in the art.

Linkers

In a further aspect, the phospholinked nucleotides of the invention comprise a nucleotide joined to a bead through a linker (represented by the group "$R_2$" in Formula (I) provided above). Those of skill in the art will appreciate that a linker can be of any form that is suitable to bind to the bead and to the nucleoside polyphosphate, thereby "linking" the two molecules together. It will be appreciated that linkers of use in the invention are linkers that provide an adequate distance between the nucleotide and the bead to avoid interactions between the bead and a polymerase. As the bead is generally of larger size than a polymerase, the bead could hinder incorporation of the labeled nucleotide during a nucleic acid synthesis reaction if it were too close to the polymerase.

Generally, a linker will be formed from a molecule comprising reactive functional groups that are complementary to functional groups on the surface of the bead and/or the nucleoside polyphosphate, thereby forming the necessary bonds. As used herein, the term "linker" and "linker moiety" are used interchangeably.

In an exemplary aspect, linkers of the invention can be selected from substituted or unsubstituted alkyl (such as alkane or alkene linkers of from about C20 to about C30), substituted or unsubstituted heteroalkyl, substituted or unsubstituted aryl, substituted or unsubstituted heteroaryl, substituted or unsubstituted cycloalkyl, and substituted or unsubstituted heterocycloalkyl. In a further aspect, linkers of the invention may include poly(ethylene glycol) (PEG) groups, saturated or unsaturated aliphatic structures comprised of single or connected rings, amino acid linkers, peptide linkers, nucleic acid linkers, PNA, LNA, as well as linkers containing phosphate or phosphonate groups. Examples of some of these linker types are described in e.g., Provisional U.S. Patent Application No. 61/069,247, filed Mar. 13, 2008, which is incorporated herein by reference in its entirety for all purposes and in particular for all teachings related to linkers.

Figure 2:
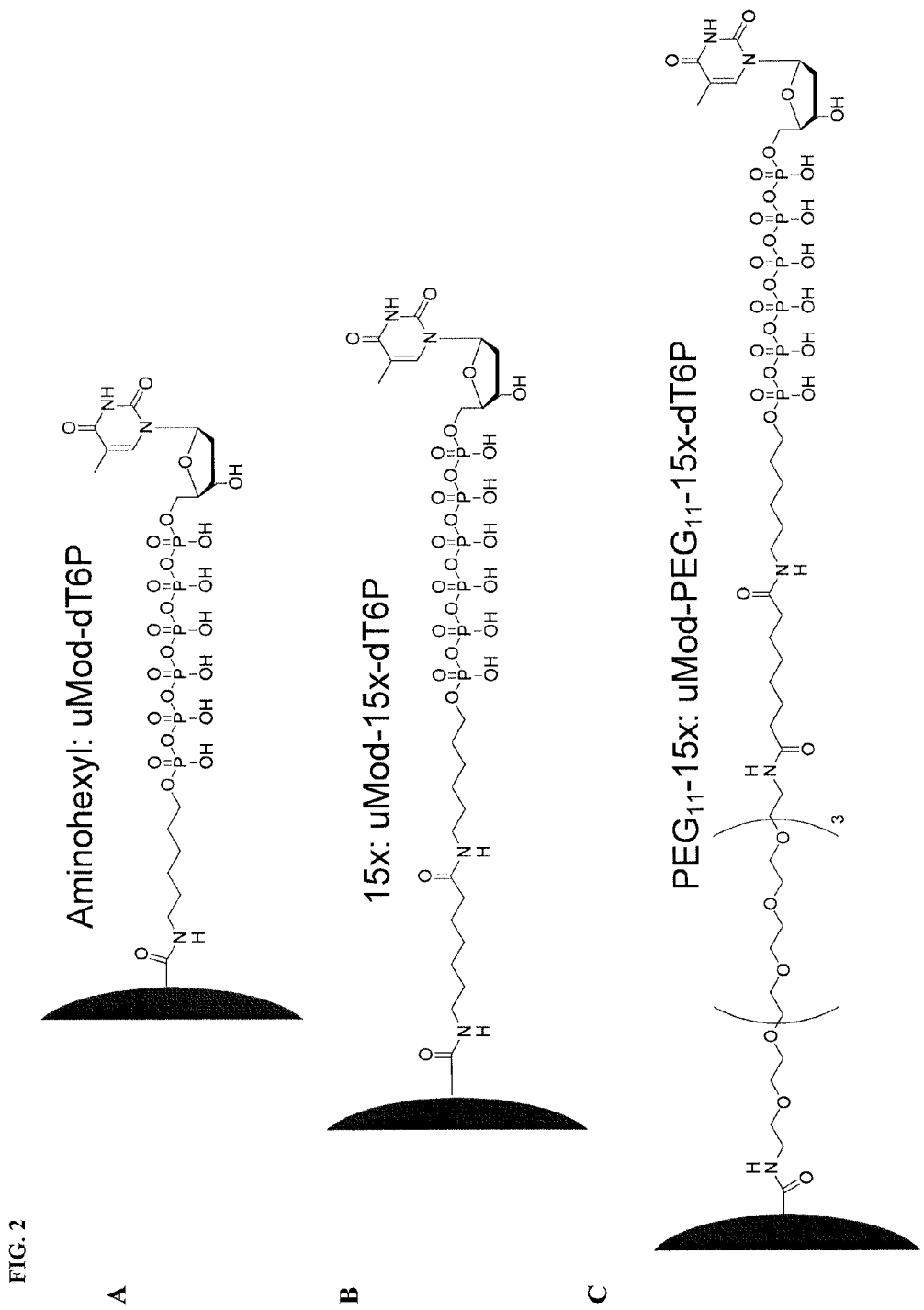
FIG. 2 illustrates different bead-labeled phospholink nucleotides with linkers of different length and structure.

As illustrated in FIG. 2, a variety of linkers can be used in accordance with the invention. The structures in FIG. 2 are exemplary and are not meant to be limiting as to the linking moieties that can be used in accordance with the invention. Such linkers may include aminohexyl groups (FIGS. 2A and B) and/or chains of poly(ethylene glycol) groups (FIG. 2C). In a further embodiment, a combination of structures such as those illustrated in FIG. 2 are used as linkers in accordance with the invention.

Figure 3:
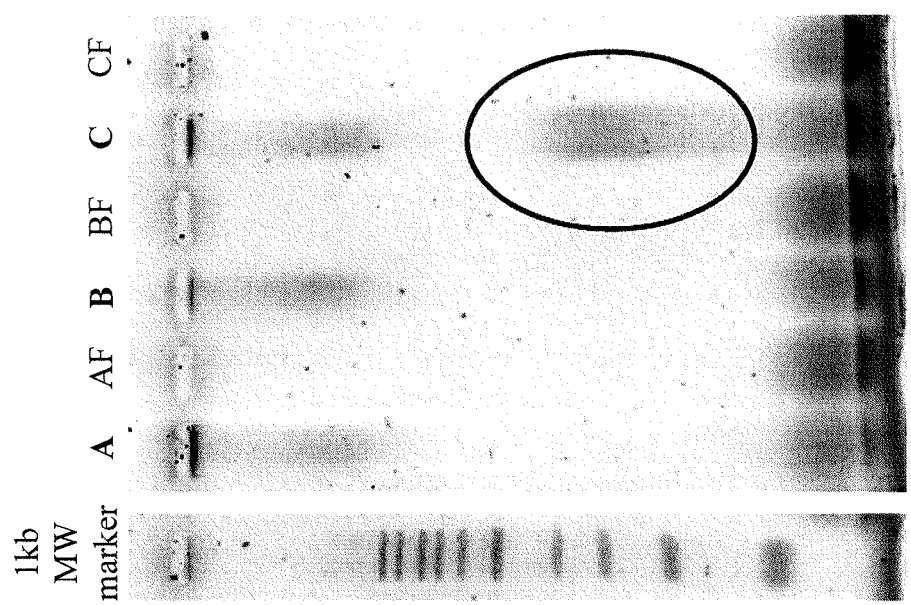
FIG. 3 shows the results of a DNA incorporation experiment with bead-labeled phospholink nucleotides. The lanes marked A, B and C show the results from DNA incorporation experiments using bead-labeled phospholink nucleotides with the structures in FIGS. 2A, 2B and 2C respectively. The lanes marked AF, BF and CF are control lanes.

In one aspect of the invention, an appropriate linker for a sequencing application is identified through assays for phospholink nucleotide incorporation in bulk DNA synthesis assays. The results of one such assay are shown in FIG. 3. Among those tested, the linker that allowed successful incorporation of the phospholink nucleotide (as shown in lane "C") was the linker that contained a chain comprising multiple poly(ethylene glycol) moieties. The structure of this linker is illustrated in FIG. 2C. The other two linkers illustrated in FIGS. 2A and B were not successful in allowing incorporation of the labeled nucleotide (see lanes A and B of FIG. 3).

In one embodiment, the linker is a member selected from substituted or unsubstituted alkyl, substituted or unsubstituted heteroalkyl, substituted or unsubstituted aryl, substituted or unsubstituted heteroaryl, substituted or unsubstituted cycloalkyl, and substituted or unsubstituted heterocycloalkyl. In one example, the linker is selected from straight- and branched carbon-chains, optionally including at least one heteroatom (e.g., at least one functional group, such as ether, thioether, amide, sulfonamide, carbonate, carbamate, urea and thiourea), and optionally including at least one aromatic, heteroaromatic or non-aromatic ring structure (e.g., cycloalkyl, phenyl).

The linker as a whole may comprise a single covalent bond or a series of stable bonds. Thus, a reporter molecule (such as a fluorescent bead) may be directly attached to another reactant, such as a nucleoside polyphosphate, or the reporter molecule may be attached to a nucleoside polyphosphate through a series of stable bonds. A linker that is a series of stable covalent bonds can incorporate non-carbon atoms, such as nitrogen, oxygen, sulfur and phosphorous, as well as other atoms and combinations of atoms, as is known in the art.

If the linker is not directly attached to a phospholink nucleotide and/or a bead by a single covalent bond, the attachment may comprise a combination of stable chemical bonds, including for example, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds.

Removal of Non-labeled Nucleotides

In a further aspect of the invention, nucleotides that are not successfully joined to a bead are separated from the bead-labeled nucleotides using methods known in the art, including dialysis, HPLC, membrane filtration and size exclusion chromatography. Removing the non-labeled nucleotides avoids having such nucleotides incorporated into a nascent strand during a polymerase-mediate nucleic acid synthesis reaction, thus avoiding a missed incorporation events in sequencing applications based on detecting such incorporated nucleotides.

In one exemplary embodiment, nucleotides that are not joined to a bead are removed by centrifugation through a membrane which is sized to permit the non-labeled nucleotides to pass through, whereas the bead-labeled nucleotides are retained. In an exemplary embodiment, a 100 kDa MW cutoff membrane is used to remove non-labeled nucleotides before the labeled phospholink nucleotides are used in sequencing applications. In a further exemplary embodiment, the purification of labeled phospholink nucleotides can be monitored by measuring the absorbance of the flowthrough after several cycles of washes and centrifugation through a 100 kDa MW cutoff membrane.

In another exemplary embodiment, a phosphodiesterase enzyme is used to remove nucleotides that are not joined to beads according to the invention. The phosphodiesterase will break phosphodiester bonds. Nucleotides joined to beads can be protected from the action of the phosphodiesterase through encapsulation, or separation by a membrane with a molecular weight cutoff that only lets nucleotides, but not beads, diffuse through. In particular, reaction systems may be equipped with partitioned regions that contain in one region a nucleic acid synthesis complex and bead bound nucleotides, while in the other region is disposed a phophodiesterase enzyme. The two regions are separated by a semipermeable barrier, e.g., a membrane or the like, that allows for free diffusion of free nucleotides into the region containing the phosphodiesterase, but does not allow those nucleotides that remain bound to the beads to enter this region, or allow the phosphodiesterase to enter the region in which the synthesis complex and bead bound nucleotides are disposed. The result is that bead bound nucleotides remain within the reaction region occupied by the synthesis complex, while unbound nucleotides freely diffuse into the phophodiesterase region and are consumed by the enzyme. The phosphodiesterase enzyme may be used in combination with the washing/centrifugation methods described above for removing nucleotides not joined to beads.

In another exemplary embodiment, excess unbound nucleotides are removed by dialysis methods. Such methods are well known in the art.

Sequencing Applications Utilizing Phospholink Nucleotides

Phospholink nucleotides of the invention are particularly useful in sequencing applications, particularly so-called "single molecule" sequencing applications. Bead-labeled phospholink nucleotides provide several advantages over traditional methods of labeling nucleotides, including elimination and/or alleviation of photodamage, and increasing accuracy by increasing label brightness Single molecule sequencing applications are well known and well characterized in the art. See, e.g., Rigler, et al., DNA-Sequencing at the Single Molecule Level, Journal of Biotechnology, 86(3): 161 (2001); Goodwin, P. M., et al., Application of Single Molecule Detection to DNA Sequencing. Nucleosides & Nucleotides, 16(5-6): 543-550 (1997); Howorka, S., et al., Sequence-Specific Detection of Individual DNA Strands using Engineered Nanopores, Nature Biotechnology, 19(7): 636-639 (2001); Meller, A., et al., Rapid Nanopore Discrimination Between Single Polynucleotide Molecules, Proceedings of the National Academy of Sciences of the United States of America, 97(3): 1079-1084 (2000); Driscoll, R. J., et al., Atomic-Scale Imaging of DNA Using Scanning Tunneling Microscopy. Nature, 346(6281): 294-296 (1990).

Other methods of single molecule sequencing known in the art include detecting individual nucleotides as they are incorporated into a primed template, i.e., sequencing by synthesis. Such methods often utilize exonucleases to sequentially release individual fluorescently labelled bases as a second step after DNA polymerase has formed a complete complementary strand. See Goodwin et al., "Application of Single Molecule Detection to DNA Sequencing," Nucleos. Nucleot. 16: 543-550 (1997).

The present invention applies equally to sequencing all types of nucleic acids (DNA, RNA, DNA/RNA hybrids etc.) using a number of polymerizing enzymes (DNA polymerases, RNA polymerases, reverse transcriptases, mixtures, etc.). Therefore, appropriate nucleotide analogs serving as substrate molecules for the nucleic acid polymerizing enzyme can consist of members of the groups of dNTPs, NTPs, modified dNTPs or NTPs, peptide nucleotides, modified peptide nucleotides, or modified phosphate-sugar backbone nucleotides.

As discussed herein, the brighter and more robust signals provided by the bead-labeled phospholink nucleotides of the invention reduce the number of false negatives in a sequencing reaction. In addition, the brighter signals can enable the use of a faster camera, which can increase the accuracy of detection in such sequencing reactions. The shorter residence time events can be more accurately detected with faster cameras, particularly since the brighter signal allows the shorter residence time events to be detected over background.

Template-Dependent Nucleic Acid Synthesis

The present invention is of particular use in sequencing methods based on template-dependent nucleic acid synthesis. In such methods, one or more nucleotides are introduced to a template primer complex in the presence of polymerase. Template-dependent nucleotide incorporation takes place as the primer (also referred to herein as the "nascent strand") is elongated. Such nucleotides are generally labeled, and each nucleotide incorporated into the nascent strand can be detected using that label.

During or after each labeled nucleotide is added to the sequencing primer, the nucleotide added to the sequencing primer is identified. This is most generally achieved by giving each nucleotide a different distinguishable label. By detecting which of the different labels are added to the sequencing primer, the corresponding nucleotide added to the sequencing primer can be identified and, by virtue of its complementary nature, the base of the target nucleic acid which the nucleotide complements can be determined. Once this is achieved, it is no longer necessary for the nucleotide that was added to the sequencing primer to retain its label. In fact, the continued presence of labels on nucleotide complementing bases in the target nucleic acid that have already been sequenced would very likely interfere with the detection of nucleotide analogs subsequently added to the primer. Accordingly, labels added to the sequencing primer are generally removed after they have been detected. This preferably takes place before additional nucleotides are incorporated into the oligonucleotide primer.

The labeled phospholink nucleotides of the present invention are of particular use in such sequencing-by-synthesis applications, because, as discussed further herein, the fluorescent beads used in the invention provide a much brighter signal than is possible with traditional methods of labeling nucleotides for such applications. This brighter signal improves the accuracy of such sequencing-by-synthesis applications by reducing the number of incorporation events that go undetected. In addition, since each bead is joined to multiple phospholink nucleotides, each bead can be recycled through multiple incorporation events, thus reducing the amount of reagents needed in a particular sequencing-by-synthesis reaction.

In one aspect, the labeled phospholink nucleotides of the invention are utilized in polymerase reactions isolated within extremely small observation volumes, such as zero-mode waveguides, as described for example in U.S. Pat. Nos. 6,917, 726 and 7,056,661, each of which is hereby incorporated by reference in its entirety for all purposes, and in particular for teaching related to zero-mode waveguides and sequencing applications utilizing such zero-mode waveguides.

Sequencing Applications Utilizing Flow Cells

In one aspect, the phospholinked nucleotides of the present invention can be used in conjunction with a sequencing system that utilizes a flow cell. In such an aspect of the invention, fluorescent bead-labeled phospholinked nucleotides and a microfluidic flow cell are used to detect incorporation of labeled substrates into the nascent strand. In an exemplary embodiment, a polymerase is immobilized at a stationary location in the flow cell relative to the remaining solution, which has a constant fluid flow velocity. In a further embodiment, the polymerase is immobilized on a surface of the flow cell and a solution containing bead-labeled phospholink nucleotides are flowed over the polymerase at a constant velocity. The polymerase will temporarily retain a bead-labeled phospholink nucleotide complementary to a nucleotide of the template strand. This temporary retention of the labeled phospholink nucleotide will be detectable relative to the remaining solution moving at a constant fluid flow velocity around the polymerase. Thus, the residence time in such a system is not measured by the absence or presence of a label in a detection volume, but by the intermittent discontinuation of movement of the label as the phospholink nucleotide is held in the active site of the polymerase.

In one embodiment, four differentially labeled phospholink nucleotides are used in such flow cell reactions, and a complementary base of the template will be identified by identifying a temporarily retained bead.

In a further embodiment, different nucleotides will be labeled with beads comprising the same fluorophore, but the size of the bead will differ with regards to the identity of the nucleotide. For example, adenosine polyphosphates can be linked to smaller beads, whereas guanosine polyphosphates are linked to larger beads. The diffusion properties before and after retention to the polymerase will thus differ, and the residence time combined with the diffusion kinetics of the temporarily retained bead-labeled phospholink nucleotide will provide the identity of the phospholink nucleotide (and thus the complementary nucleotide on the template nucleic acid). Different sizes of beads will also differ by the number of encapsulated fluorophores, corresponding to different relative brightness, which can further aid in distinguishing the different nucleotides coupled to beads of different sizes.

In a still further embodiment, detection of the temporarily retained bead is accomplished using imaging methods known in the art, for example total-internal reflection fluorescence (TIRF) microscopy.

Nucleic Acid Sequencing Systems

In one aspect, the labeled phospholink nucleotides of the invention are used in a nucleic acid sequencing system. Such a system can include elements for conducting a sequencing-by-synthesis reaction in a single module or device, or in a series of connected modules or devices. In a further aspect, such a nucleic acid sequencing system can include a body structure comprising a plurality of microfluidic channels. Such a system can further include a source of one or more template nucleic acid, which template nucleic acid source is capable of being fluidly coupled to at least a first one of the microfluidic channels and a source of one or more sequencing reagents, which sequencing reagent source is capable of being fluidly coupled to the at least first microfluidic channel. In a still further aspect, the source of the one or more sequencing reagent can comprise a set of at least four differently labeled phospholink nucleotides of the invention, which, as discussed further herein, can in one embodiment include a fluorescent bead. In one exemplary embodiment, the system further includes a fluid flow controller that flows the template nucleic acid and the one or more sequencing reagents into contact in the at least first microfluidic channel, whereby one or more sequencing product is formed. In a still further embodiment, a detector detects the one or more sequencing product, thereby determining at least a subsequence of the template nucleic acid.

Kits

The present invention further provides kits useful for exploiting the labeled phospholink nucleotides described herein in a number of applications. In a first aspect, such kits will generally include the labeled phospholink nucleotides of the invention packaged in a fashion to enable their use, and preferably, a set of at least four different phospholink nucleotides of the invention, namely those that are analogous to A, T, G and C, where each bears a detectably different label to permit its individual identification in the presence of the others. Depending upon the desired application, the kits of the invention may further include additional reagents, such as enzymes (including polymerase enzymes) for performing template dependent synthesis reactions employing phospholink nucleotides of the invention, a control sequence, and other reagents, including buffer solutions and/or salt solutions, including, e.g., divalent metal ions (such as $Mg^{2+}$, $Mn^{2+}Ca^{2+}$, $Co^{2+}$, $Ba^{2+}$, $Sr^{2+}$ and/or $Fe^{2+}$), and standard solutions (such as dye standards for detector calibration). Such kits can also include instructions for use of the phospholink nucleotides and other reagents in accordance with the desired application methods, e.g., nucleic acid sequencing, and the like.

EXAMPLES

Example 1

Coupling of Nanosphere Label to Phospholink Nucleotide

As illustrated in FIG. 1, a nanosphere with a surface derivatized with carboxyl groups was activated with 1-ethyl-3-(3-dimethylaminopropyl) carbodiimide to form an intermediate acetic N'-(3-(dimethylamino)propyl)-N-ethylcarbamidic anhydride compound, which, when contacted with a nucleoside polyphosphate, will result in a bond between the terminal phosphate of the thymine hexaphosphate and the activated functional group of the nanosphere. In the case of the illustration in FIG. 1, the nucleoside polyphosphate is a thymine hexaphosphate, but it will be appreciated that any nucleoside polyphosphate could be used in accordance with this method.

In one exemplary embodiment, 1.68 µM 25 nm micromod Red nanoparticles (micromod Partikeltechnologie GmbH, Rostock, Germany) and 168 µM $NH_2$-$PEG_{12}$-15x-dC6P (100 fold excess) were mixed in 25 mM MES buffer. 0.37 mg of EDC (5000 fold molar excess) were added while vortexing the solution, followed by incubation for one hour at room temperature.

Optionally, NHS or sulfo-NHS can be included in the reaction (e.g., also at 5000 fold excess) to stabilize the amine-reactive intermediate by converting it to an amine-reactive Sulfo-NHS ester, thus increasing the efficiency of EDC-mediated coupling reactions (see Grabarek, Z. and Gergely, J. (1990), *Analyt Biochem*, 185:131-135 and Staros and Swing (1986) *Analyt Biochem*, 156: 220-222, each of which is hereby incorporated by reference in its entirety for all purposes and in particular for all teachings related to coupling reactions as described above.

Example 2

Determining Spacing Necessary Between Bead Label and Nucleotide

In order to determine the optimal distance between the bead and the nucleoside polyphosphate, multiple different linkers were tested in an incorporation reaction. FIG. 3 displays the results from one such reaction. Of the three different linkers tested (A, B and C), only the nucleotide attached to a bead through linker C was successfully incorporated by the polymerase. The structures of the three different linkers A, B, and C are illustrated in FIGS. 2A, B, and C respectively. In these particular experiments, the polymerase used was Φ29 DNA polymerase.

The following reagents were mixed (to final concentrations): 50 mM ACES buffer, pH 7.1, 75 mM potassium acetate, 5 mM DTT, 0.7 mM manganese acetate, 100 nM circular single-stranded, primed DNA template, and Φ29 DNA polymerase. The mixture was incubated for 10 minutes on ice, and then nucleotides and bead-conjugated nucleotides were added as appropriate to a 5 µM final concentration. The mixture was then incubated for 15 minutes at room temperature and then run on an 0.8% agarose gel with a 1 kb molecular weight marker as a calibration lane. The gel was stained with SybrGold nucleic acid stain and then imaged. Lanes AF, BF and CF in FIG. 3 depict absence of DNA polymerization when the 7th flowthrough (see FIG. 5) is used instead of the bead-conjugated nucleotide, proving the absence of free nucleotides in the bead sample solution.

Example 3

Diffusion Time of Particles in Zero-mode Waveguides

Figure 4:
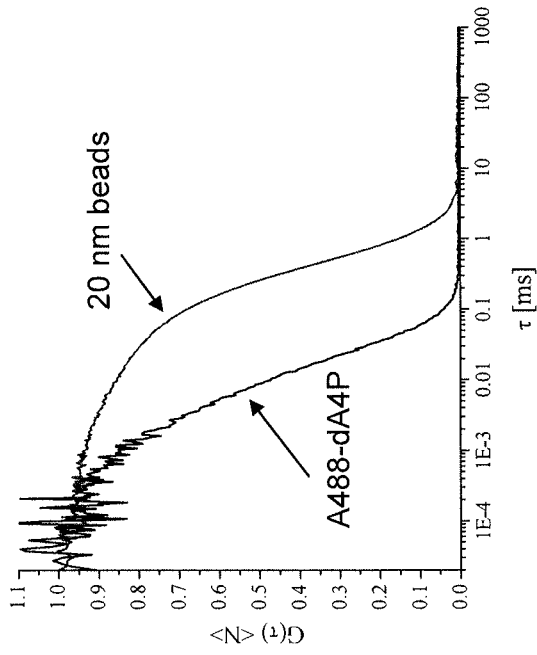
FIG. 4 shows the diffusion times of bead-labeled phospholink nucleotides and unconjugated beads in zero-mode waveguides with diameters of (A) 80 nm and (B) 120 nm.
Figure 4:
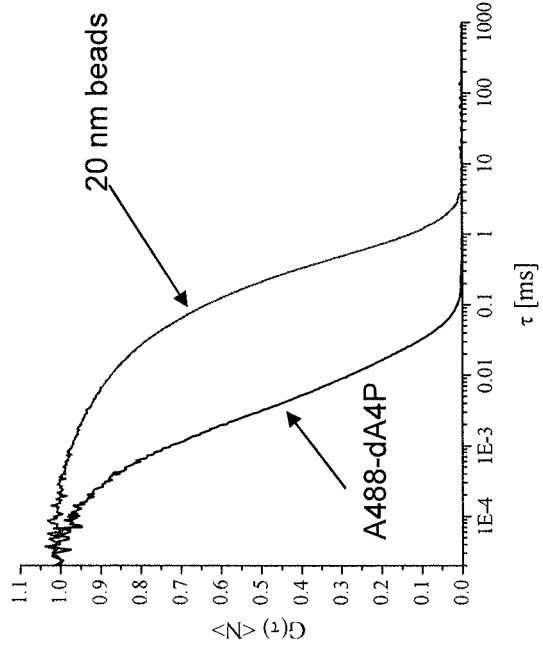

FIG. 4 shows the results of experiments measuring the diffusion times of unbound beads and beads linked to phospholink nucleotides. FIG. 4A shows the difference in diffusion times between the plain beads and the beads linked to adenosine tetraphosphate (A488-dA4P) in a zero-mode waveguide (ZMW) of with a diameter of 80 nm. FIG. 4B shows the results of similar measurements conducted in a ZMW with a diameter of 120 nm. These experiments show that the diffusion time decay for both the bare beads and the bead-labeled phospholink nucleotides are both complete between 1 and 10 milliseconds, which allows for a temporal differentiation between diffusion and incorporation events. Polymerase incorporation generally occurs in the 10 to 100 ms time scale.

Example 4

Purification Bead-labeled Phospholink Nucleotides

In order to avoid incorporation of nucleotides that are not labeled according to the present invention, in one embodiment the invention provides methods for purifying bead-labeled phospholink nucleotides.

One way to purify the labeled nucleotides is through repeated washing and centrifugation through a 100 kDa MW cutoff membrane. The flowthrough absorbance can be measured to monitor the purity.

Figure 5:
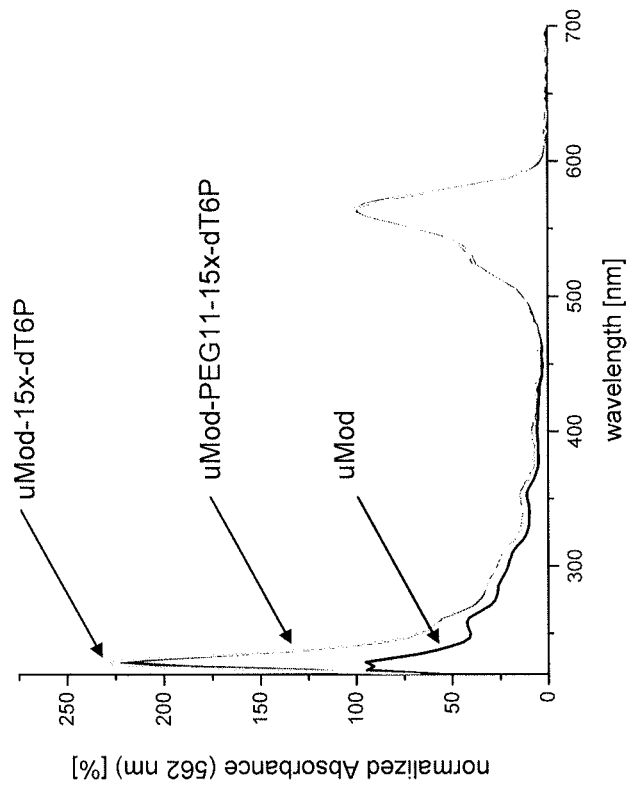
FIG. 5 shows results from measurements of flowthrough absorbance.
Figure 5:
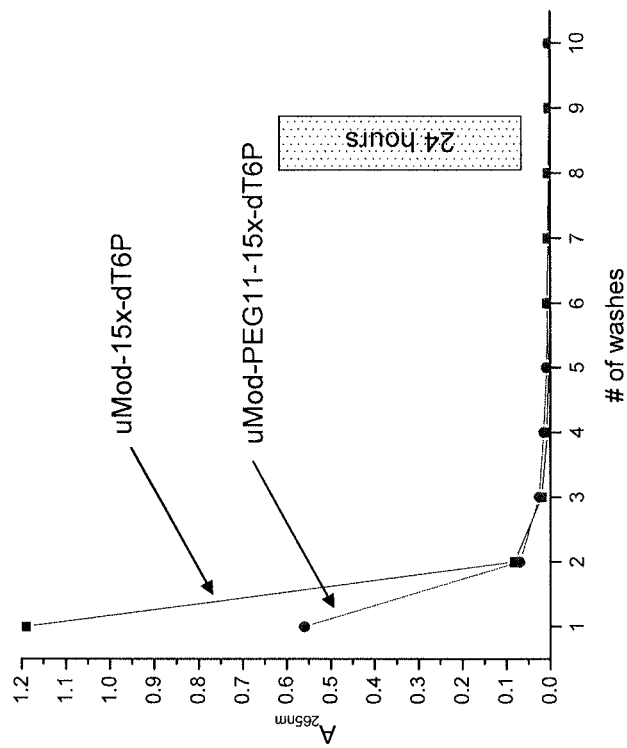

The results of one such experiment are provided in FIG. 5. FIG. 5A shows the flowthrough absorbance as a function of number of washes. FIG. 5B shows the absorbance spectrum of three different types of bead-labeled nucleotides. The peak on the right of FIG. 5B represents the absorption spectrum of the bead-encapsulated fluorescent dye, and the peak and shoulder on the left side of the graph correspond to both absorption of fluorescent dye and nucleotide. The arrow in FIG. 5B points to the difference in absorbance between unconjugated and nucleotide-conjugated beads. Excess absorbance in this area indicates the presence of bead-conjugated nucleotides in the sample.

The difference between the absorbance of "bare" particles to those joined to phospholink nucleotides can provide a quantitative estimate of the nucleotide/bead ratio, using the maximum absorption wavelengths for both the dye and the nucleotide. Table I provides exemplary data for calculating such a ratio. For example, the absorbance of the stock particles can be measured at two different wavelengths ("A565 of stock" and "A267 of stock"). The absorbance of particles joined to phospholink nucleotides can be measured at the same two wavelengths. In Table I, the phospholink nucleotides measured are deoxythymine hexaphosphate analogs joined to beads through a "uMod-PEG11-15x" linker, the structure of which is shown in FIG. 2C. using the dye absorbance to calculate the concentration of beads in the two samples, and the corresponding expected absorbance at 267 nm (the maximum absorbance of the nucleotide), the excess absorbance at 267 nm for the nucleotide-conjugated sample is used to calculate the concentration of nucleotides in the sample (using the known extinction coefficient for dTTP). The ratio between the concentration of nucleotide to concentration of beads yields the number of nucleotides per bead.

TABLE I

| Particle stock concentration (from manufacturer) | 5.50E+15 particles/ml |
| particle stock dilution | 0.5 |
| particle stock concentration | 4.58 uM |
| A565 of stock | 0.366 |
| A267 of stock | 0.135 |
| A565 of uMod-PEG11-15x-dT6P | 0.701 |
| A267 of uMod-PEG11-15x-dT6P | 0.324 |
| uMod-PEG11-15x-dT6P particle concentration | 8.78 uM |
| corresponding A267 from that concentration | 0.259 |
| A267 from dT6P on uMod-PEG11-15x-dT6P | 0.065 |
| concentration of dT6P on uMod-PEG11-15x-dT6P | 68.16 uM |
| ratio of dT6P/particles | 7.76 |

Example 5

Flat-glass Photodamage Assay

The effects of photodamage on bare particles (also referred to herein as "beads" or "nanospheres") and on particles joined to phospholink nucleotides was measured in a flat-glass photodamage assay, in which DNA polymerase/DNA template complexes are immobilized on a glass surface, and irradiated with laser illumination while DNA synthesis is taking place with fluorescence-labeled or bead labeled nucleotides. Thereafter, the presence or absence of active DNA polymerase is probed by DNA synthesis using a base-linked nucleotide (e.g. ChromaTide-Alexa-Fluor 488-dUTP, Invitrogen Corp., Carlsbad, Calif.), and subsequent bright-field microscopy imaging of the surface. Undamaged polymerase incorporates the base-linked nucleotide into DNA, yielding fluorescence signal from the surface, whereas polymerase damaged by laser illumination during the synthesis period with bead-conjugated analog would be inactive, thereby rendering the illuminated region dark after the chromatide "development" step. No damage was seen for either the bare particles or for particles joined to phospholink nucleotides under reaction conditions in which oxygen was removed (e.g., by the use of oxygen scavenging systems known in the art, such as the glucose oxidase/catalase system, or the protocatechuic acid deoxygenase system). Damage was observed in oxygen conditions at 5 $\mu W/\mu m^2$, but the bead-labeled nucleotides were 10 times brighter than A532 and 20 times brighter than A568. This drastically improved brightness means that less laser power can be used in sequencing reactions, resulting in less damage to the polymerase.

Although described in some detail for purposes of illustration, it will be readily appreciated that a number of variations known or appreciated by those of skill in the art may be practiced within the scope of present invention. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes.

What is claimed:

1. A method of determining an identity of a nucleotide in a template nucleic acid sequence, said method comprising:
   a. providing said template nucleic acid sequence complexed with a polymerase enzyme capable of template dependent synthesis of a complementary nascent sequence as a first complex;
   b. contacting said first complex with a labeled phospholink nucleotide, wherein said labeled phospholink nucleotide comprises a bead comprising at least one fluorophore, wherein said bead is encapsulated in an organic, inorganic, or polymeric material, and wherein said labeled phospholink nucleotide is complementary to a known nucleotide; and
   c. detecting whether said labeled phospholink nucleotide is incorporated into said nascent sequence, wherein incorporation of said labeled phospholink nucleotide is indicative that said complementary nucleotide is in a position in the template nucleic acid that is being processed by the polymerase enzyme.

2. The method of claim 1, wherein said first complex is contained in a microfluidic flow cell.

3. The method of claim 2, wherein said microfluidic flow cell comprises a surface, and wherein said polymerase of said first complex is immobilized on said surface of said microfluidic flow cell.

4. The method of claim 1, wherein said first complex is contained in a zero-mode waveguide.

5. The method of claim 1, wherein said bead comprises multiple fluorophores.

6. The method of claim 5, wherein said detecting step comprises detecting a signal from said bead comprising multiple fluorophores, and wherein said signal from said bead has an improved signal relative to a bead comprising a single fluorophore.

7. The method of claim 1, wherein multiple nucleotides are attached to said bead.

8. The method of claim 7, wherein subsequent to said detecting step, said method further comprises cleaving said bead from said phospholink nucleotide incorporated into said nascent sequence.

9. The method of claim 8, wherein said providing, contacting, detecting and cleaving steps are repeated a number of times to identify a desired number of nucleotides in said template nucleic acid sequence.

10. The method of claim 1, wherein said labeled phospholink nucleotide comprises a structure that has a formula:

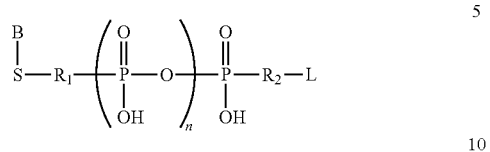

wherein
B is a nucleobase;
S is a sugar moiety;
L is the bead;
$R_1$ is selected from oxygen and sulfur;
$R_2$ is a linker moiety; and
n is an integer selected from 0 to 9.

11. The method of claim 10, wherein said linker moiety comprises poly(ethylene glycol).

12. The method of claim 10, wherein said linker moiety is a member selected from substituted or unsubstituted alkyl, substituted or unsubstituted heteroalkyl, substituted or unsubstituted aryl, substituted or unsubstituted heteroaryl, substituted or unsubstituted cycloalkyl, and substituted or unsubstituted heterocycloalkyl.

13. The method of claim 1, wherein said bead is a latex bead.

14. The method of claim 1, wherein said bead is a fluorescent bead.

15. The method of claim 1, wherein said polymeric material is a member selected from polyethylene glycol and alginate.

* * * * *